(12) United States Patent
Lin et al.

(10) Patent No.: US 11,675,018 B1
(45) Date of Patent: Jun. 13, 2023

(54) PORTABLE BATTERY DETECTION DEVICE

(71) Applicant: NATIONAL CHUNG SHAN INSTITUTE OF SCIENCE AND TECHNOLOGY, Taoyuan (TW)

(72) Inventors: Dao-Qin Lin, Taoyuan (TW); Wei-Min Hsiao, Taoyuan (TW); Shih-Chang Tseng, Taoyuan (TW); Chih-Hsien Chung, Taoyuan (TW); Gwo-Huei You, Taoyuan (TW); Kuo-Kuang Jen, Taoyuan (TW)

(73) Assignee: NATIONAL CHUNG SHAN INSTITUTE OF SCIENCE AND TECHNOLOGY, Taoyuan (TW)

( * ) Notice: Subject to any disclaimer, the term of this patent is extended or adjusted under 35 U.S.C. 154(b) by 0 days.

(21) Appl. No.: 17/564,264

(22) Filed: Dec. 29, 2021

(51) Int. Cl.
| | |
|---|---|
| G01R 31/389 | (2019.01) |
| G01K 13/00 | (2021.01) |
| G01R 31/367 | (2019.01) |
| G01R 27/02 | (2006.01) |
| G01N 33/00 | (2006.01) |

(52) U.S. Cl.
CPC .......... *G01R 31/389* (2019.01); *G01K 13/00* (2013.01); *G01N 33/0027* (2013.01); *G01R 27/02* (2013.01); *G01R 31/367* (2019.01)

(58) Field of Classification Search
None
See application file for complete search history.

(56) References Cited

U.S. PATENT DOCUMENTS

| | | | | |
|---|---|---|---|---|
| 6,988,053 | B2 * | 1/2006 | Namaky | G01R 31/007 324/426 |
| 2008/0030198 | A1 * | 2/2008 | Kawata | G01R 31/3842 324/426 |
| 2015/0302723 | A1 * | 10/2015 | Reade | G01R 31/371 340/636.1 |
| 2020/0355749 | A1 | 11/2020 | Takahashi et al. | |

FOREIGN PATENT DOCUMENTS

| | | |
|---|---|---|
| TW | I607226 B | 12/2017 |
| TW | I663414 B | 6/2019 |

* cited by examiner

*Primary Examiner* — Jas A Sanghera

(57) ABSTRACT

A portable battery detection device includes a battery data receiving module for receiving battery data, a temperature measurement module for measuring battery temperature, a gas measurement module for measuring discharged gas, an insulation resistance measurement module for measuring insulation resistance, a serial impedance measurement module for measuring serial impedance, a data acquisition module for receiving various data sent by the temperature measurement module and the gas measurement module, an electric meter module for measuring DC voltage, current, and impedance, the data integration module for receiving data transmitted by the battery data receiving module, the electric meter module, and the insulation resistance measurement module, and then integrating the data to the processor module, and the processor module for using data received from the data integration module, the data acquisition module, and the serial impedance measurement module to transmit data, control, and manage the operation of the portable battery detection device.

19 Claims, 4 Drawing Sheets

PORTABLE BATTERY DETECTION DEVICE

BACKGROUND OF THE INVENTION

1. Field of the Invention

The present disclosure relates to battery testing devices, and in particular to a universal portable battery system detection device for measuring, detecting, and testing various battery data and battery management system data.

2. Description of the Related Art

In order to solve environmental issues such as air pollution and fossil fuel depletion, national policies actively promote the electrification of vehicles and the development and application of various electric vehicles has become a future trend. A common requirement in the maintenance of electric vehicles is the detection of battery system failures.

Most of the commercially available battery detection devices are single-function individual detection devices (such as: HIOKI battery tester, instaligo battery tester), and measure specific problem points, or combine multiple measurement items in a fixed type to specific step detection forms by a relatively expensive integrated device (such as Chengde Technology BT 2000 Series). Although these devices are powerful, they are too bulky and cannot be easily moved. This results in frequent site problems when repairing or maintaining vehicle batteries. For example, Taiwan patent number 1607226 is an invention patent, which proposes a simple battery detection device that includes a power supply, a pressure gauge, a galvanometer, a differential circuit and a determiner; another Taiwan patent, number 1663414 is an invention patent, and proposes a device that contains a base, a line scan camera lens, and a detection drive mechanism with a cylindrical battery detection device with a line scan photographic lens set on the base; U.S. Patent Application No. US20200355749A1 proposes a device including a first sensing circuit to sense the voltage value of the secondary battery, a second sensing device sensing circuit sensing two current values of the secondary battery, and a calculation unit that uses a regression model to calculate the estimated voltage value range of the secondary battery by using an abnormality detection device.

The above-mentioned battery detection devices of the prior art are mostly single-function individual detection devices or fixed types, which are too simple in function or inconvenient to carry.

Thus, it is desirable to have improvements on the conventional battery detection devices in order to improve portability and increase functionality.

BRIEF SUMMARY OF THE INVENTION

An objective of the present disclosure is to provide a universal portable battery system detection device for measuring, detecting, and testing various battery data and battery management system data.

To achieve at least the above objective and more, the present disclosure provides a universal portable vehicle power battery system detection device, which can be easily moved, carried, and transported, and is suitable for a variety of electric vehicle batteries.

A common requirement in the maintenance of electric vehicles or electric buses is the detection of battery system failures. However, the current devices are mostly fixed-type battery detection devices that cannot be moved thereby limiting space in the facility or simple detection devices that have simple functions and do not meet actual needs. In order to solve the limitations of the fixed type device, the present disclosure develops and designs a battery detection device that is easy to carry and can be moved, which can be applied to the battery inspection and repair of electric vehicles such as electric buses and other types of electric vehicles in the future.

The present disclosure also provides a system 24V working power supply and collects Controller Area Network (CAN) data of electric vehicles and fault code judgments can be used for safety testing of various battery module data or battery management system data, including voltage, current, temperature, State Of Charge (SOC), State Of Health (SOH), carbon monoxide emissions, combustible gas, series resistance, insulation resistance, etc. that allows maintenance personnel to facilitate operation and speed up the time needed for battery maintenance.

The portable battery detection device of the present disclosure comprises a battery data receiving module to receive various data of the battery or data of the battery management system (voltage, current, temperature, SOC, SOH, etc.), and transmit the data to the data integration module and processor module. A temperature measurement module is used to measure the temperature of the battery and transmit the temperature data to a data acquisition module. A gas measurement module is used to measure the gas discharged from the battery and transfer the gas data to the data acquisition module. An insulation resistance measurement module is used to measure the insulation of the battery Impedance value, and transmit the insulation resistance value to the data integration module. A serial impedance measurement module is provided for measuring the serial impedance value of the battery, and transmit the serial impedance value to the processor. The data acquisition module is used to receive various data sent by the temperature measurement module and the gas measurement module, and transmit the battery data to the processor. An electric meter module is used to measure the battery management system circuit DC voltage, DC current, DC impedance, and transfer the data to the data integration module. A data integration module is provided for receiving the data transmitted by the battery data receiving module, the electric meter module, and the insulation resistance measurement module, and after the data is integrated, it is transmitted to the processor. The processor module uses the data transmitted by the receiving data integration module, the data acquisition module, and the serial impedance measurement module to control and manage the operation of the battery detection device. A display screen provides a human-machine interface for interacting with users and provides access to inspection data.

The battery detection device of the present disclosure is not only easy to carry, but also utilizes a variety of communication protocols such as CAN 2.0B, RS-485, USB, and can provide battery modules for voltage, temperature status, current, exhaust gas, insulation resistance, and series impedance, etc. via a plurality of connectors for safety testing. When the vehicle cannot be started or the battery has no communication signal, the battery can be tested independently by the device providing 24V working power for the battery system and reads the vehicle on-board diagnostics (OBD) data and Errorcode judgment; built-in CANbus database (DBC) corresponding decoding for different battery models in order to solve the shortcomings of the prior art, which are mostly fixed-type battery detection devices that cannot be moved and limit space, or simple-type detection devices with simple functions and detection functions that do not meet actual requirements.

To achieve at least the above objectives, the present disclosure provides a universal portable battery system detection device for detecting, measuring, and testing various battery data and battery management system data, as exemplified in any one of the above embodiments.

DETAILED DESCRIPTION OF THE INVENTION

To facilitate understanding of the object, characteristics and effects of this present disclosure, embodiments together with the attached drawings for the detailed description of the present disclosure are provided.

Figure 1:
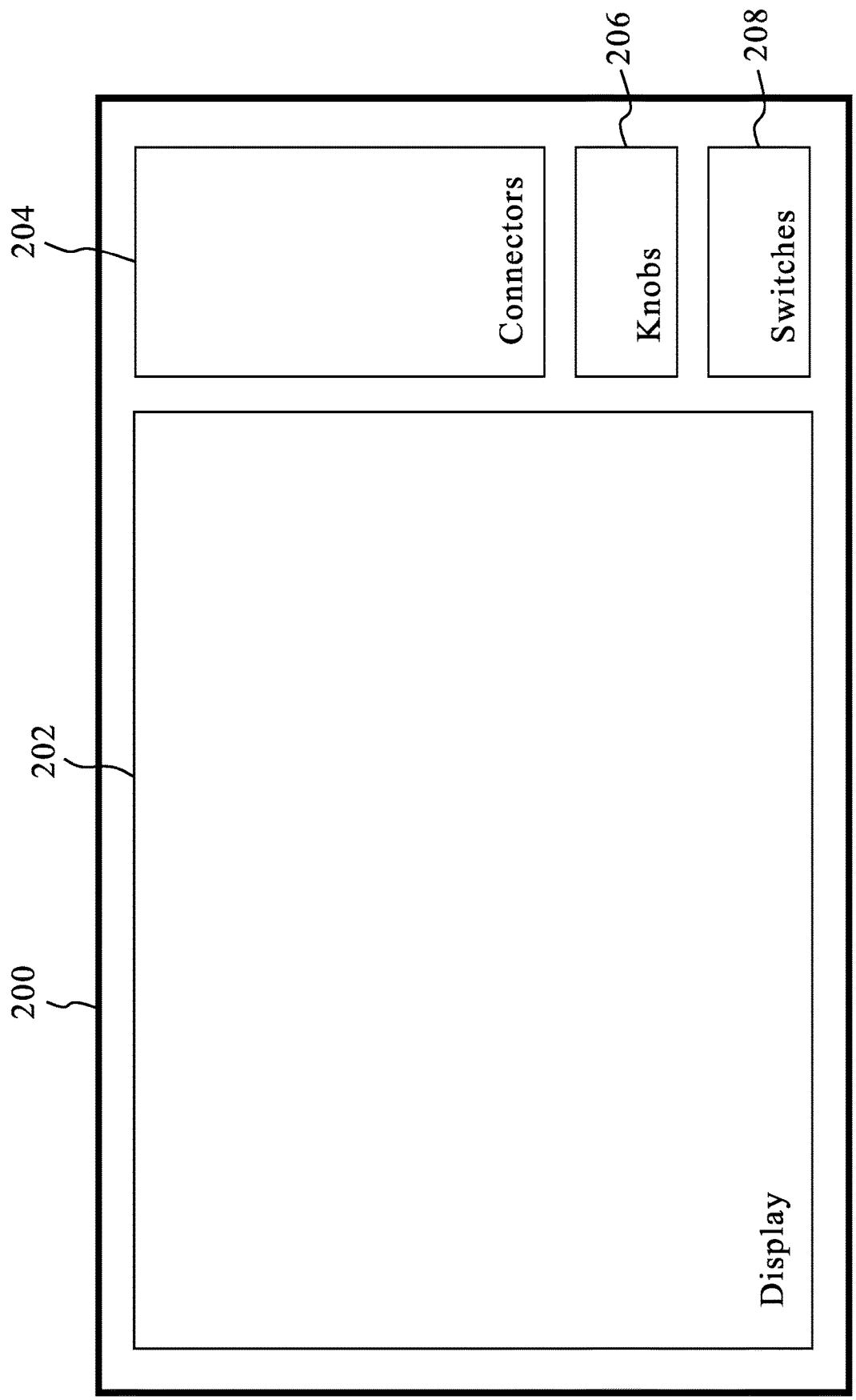
FIG. 1 is a diagram illustrating a front of a portable battery detection device according to an embodiment of the present disclosure.

Refer to FIG. 1, which is a diagram illustrating a front of a portable battery detection device according to an embodiment of the present disclosure.

The front surface of the portable battery detection device 200 of the present disclosure comprises a display 202, a connector or a plurality of connectors 204, a knob or a plurality of knobs 206, and a switch or a plurality of switches 208.

The display 202 provides a human-machine interface for interacting with users and provides access to inspection data.

The connector or plurality of connects 204 are provided to input or output signals to interface with a test battery, power, etc.

The switch or plurality of switches 208 are provided for selecting between functions such as turning on and off the portable battery detection device 200.

The technology of the present disclosure comprises a universal portable vehicle power battery system detection device 200, which can be easily moved, carried and transported, and is suitable for a variety of electric vehicle batteries. It also provides a system 24V working power supply and collects CAN data of electric vehicles and fault code judgments can be used for safety testing of various battery module data or battery management system data, including voltage, current, temperature, SOC, SOH, carbon monoxide emissions, combustible gas, series resistance, insulation resistance, etc. which allows maintenance personnel to facilitate operation and speed up the time required for maintenance.

The portable battery detection device 200 of the present disclosure is not only easy to carry, but also has a variety of communication protocols such as, for example, CAN 2.0B, RS-485, USB, etc. via the plurality of connectors 204.

The portable battery detection device 200 provides battery modules for voltage, temperature status, current, exhaust gas, insulation resistance, impedance, etc. for safety testing. When the car cannot be started or the battery has no communication signal, the battery can be tested independently. The portable battery detection device 200 provides 24V working power for the battery system and reads the vehicle detection system OBD data and Errorcode judgment. The portable battery detection device 200 comprises a built-in CANbus DBC corresponding decoding for different battery models.

The present disclosure solves the shortcomings of the prior art, which are mostly fixed-type battery detection devices that cannot be moved and limit space in a facility, or simple-type detection devices with simple functions and detection functions that do not meet actual requirements.

Figure 2:
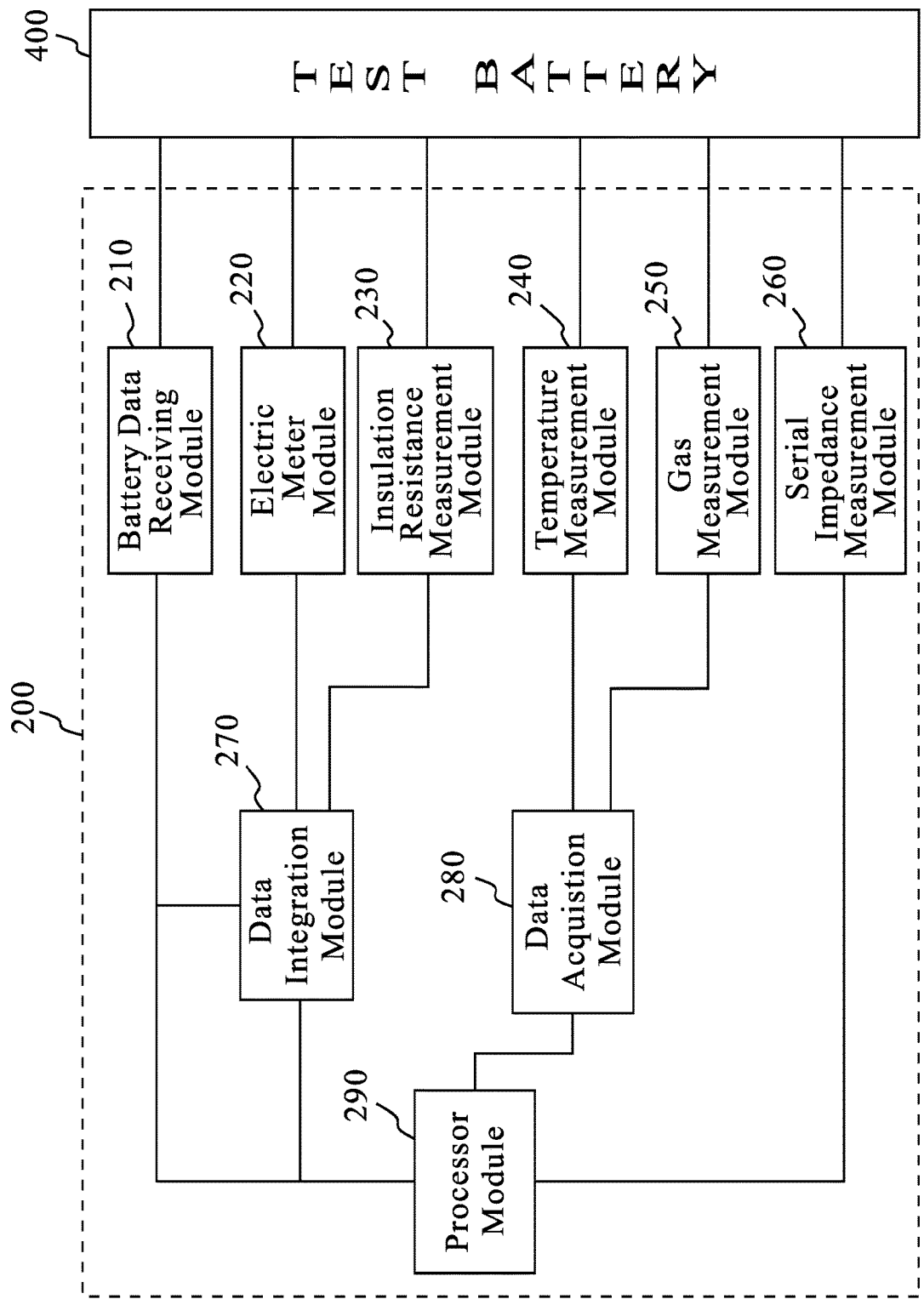
FIG. 2 is a schematic diagram illustrating a portable battery detection device according to an embodiment of the present disclosure.

Refer to FIG. 2, which is a schematic diagram illustrating a portable battery detection device according to an embodiment of the present disclosure.

The portable battery detection device 200 comprises a battery data receiving module 210, an electric meter module 220, an insulation resistance measurement module 230, a temperature measurement module 240, a gas measurement module 250, a serial impedance measurement module 260, a data integration module 270, a data acquisition module 280, and a processor module 290.

The battery data receiving module 210 is provided to receive various data of the test battery 400 or data of the battery management system (voltage, current, temperature, SOC, SOH, etc.), and transmit the data to the data integration module 270 and the processor module 290. The temperature measurement module 240 is used to measure the temperature of the test battery 400 and transmit the temperature data to the data acquisition module 280. The gas measurement module 250 is provided to measure the gas discharged from the test battery 400 and transfer the gas data to the data acquisition module 280. The insulation resistance measurement module 230 is provided to measure the insulation resistance of the battery, and transmit the insulation resistance value to the data integration module 270. The serial impedance measurement module is provided for measuring the serial impedance value of the battery 400, and transmit the serial impedance value to the processor module 290. The data acquisition module 280 is used to receive various data sent by the temperature measurement module 240 and the gas measurement module 250, and transmit the battery data to the processor module 290. The electric meter module 220 is used to measure the battery management system circuit DC voltage, DC current, DC impedance, and transfer the data to the data integration module 270. The data integration module 270 is provided for receiving the data transmitted by the battery data receiving module 210, the electric meter module 220, and the insulation resistance measurement module 230. After the data is integrated, it is transmitted to the processor module 290. The processor module 290 uses the data transmitted by the data integration module 270, the data acquisition module 280, the serial impedance measurement module 260, and the battery data receiving module 210 to control and manage the operation of the portable battery detection device 200.

Figure 3:
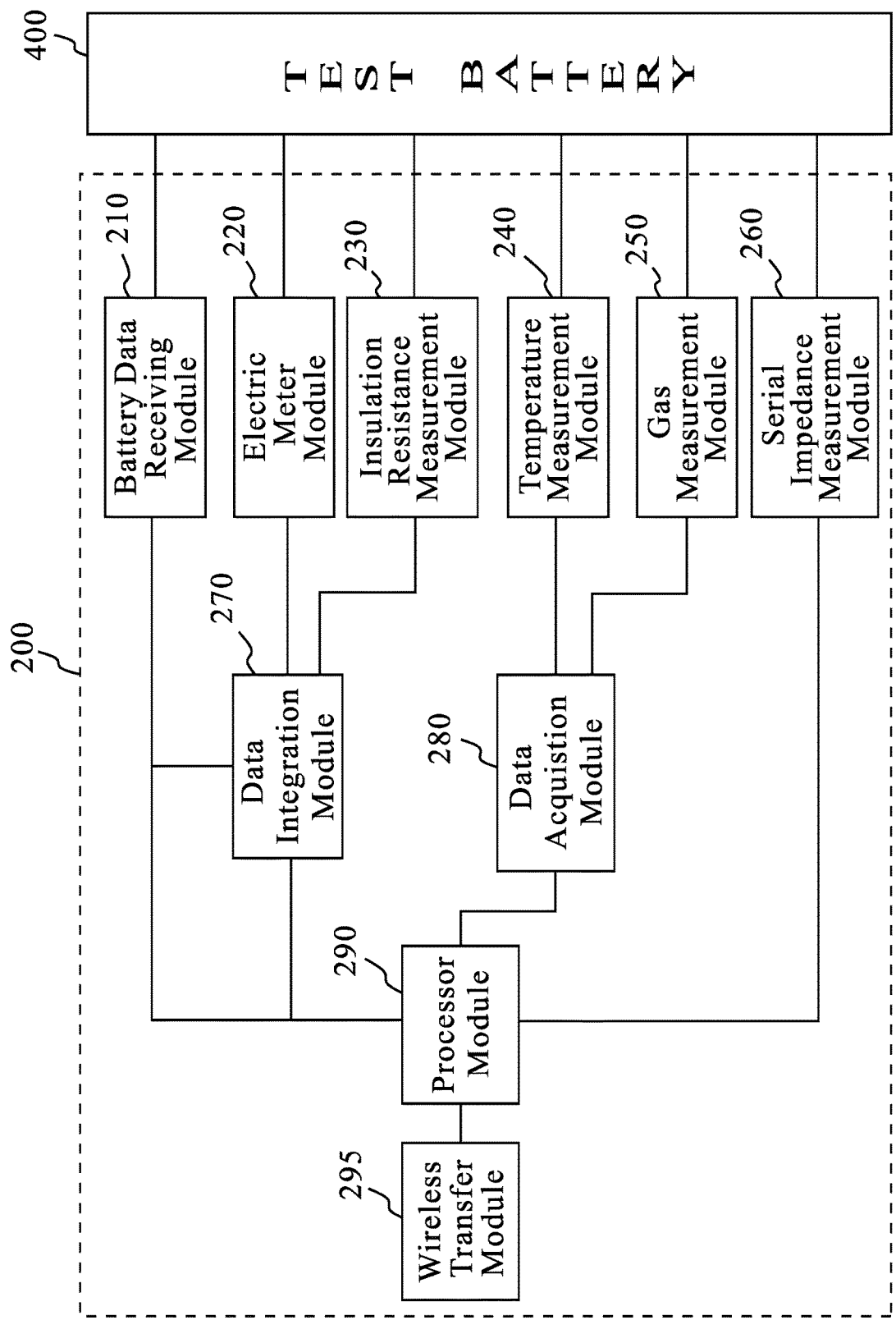
FIG. 3 is a schematic diagram illustrating a portable battery detection device according to an embodiment of the present disclosure.

Refer to FIG. 3, which is a drawing illustrating a portable battery detection device according to an embodiment of the present disclosure.

The portable battery detection device 200 of FIG. 3 is similar to the portable battery detection device 200 of FIG. 2, however, with the addition of a wireless transfer module 295.

The wireless transfer module 295 is provided for allowing the data processed by the processor module 290 to be wirelessly accessed by users or other devices.

In an embodiment of the present disclosure, the processor module 290 of the portable battery detection device 200 further comprises a data storage/output module that can output final analysis data such as, for example, reports and analysis, and can store analysis history records.

The data storage/output module of the processor module 290 can store each measurement result in a database mode, and according to the designed human-machine interface (display 202 of FIG. 1 or wireless transfer module 295 of FIG. 3), output the corresponding measurement result report, which contains the original data, analysis results, remarks . . . etc. The analysis results and remarks can be updated by software to add corresponding batteries and vehicle types.

For this function, after the charging and discharging have been completed, the portable battery detection device 200 has an independent function button to enable the database function. The historical data is arranged according to the date for users to read and review. The user can directly view the measurement results at various times through the man-machine interface, and can select the specified data output, such as, for example, output a file in Excel format for other purposes.

Figure 4:
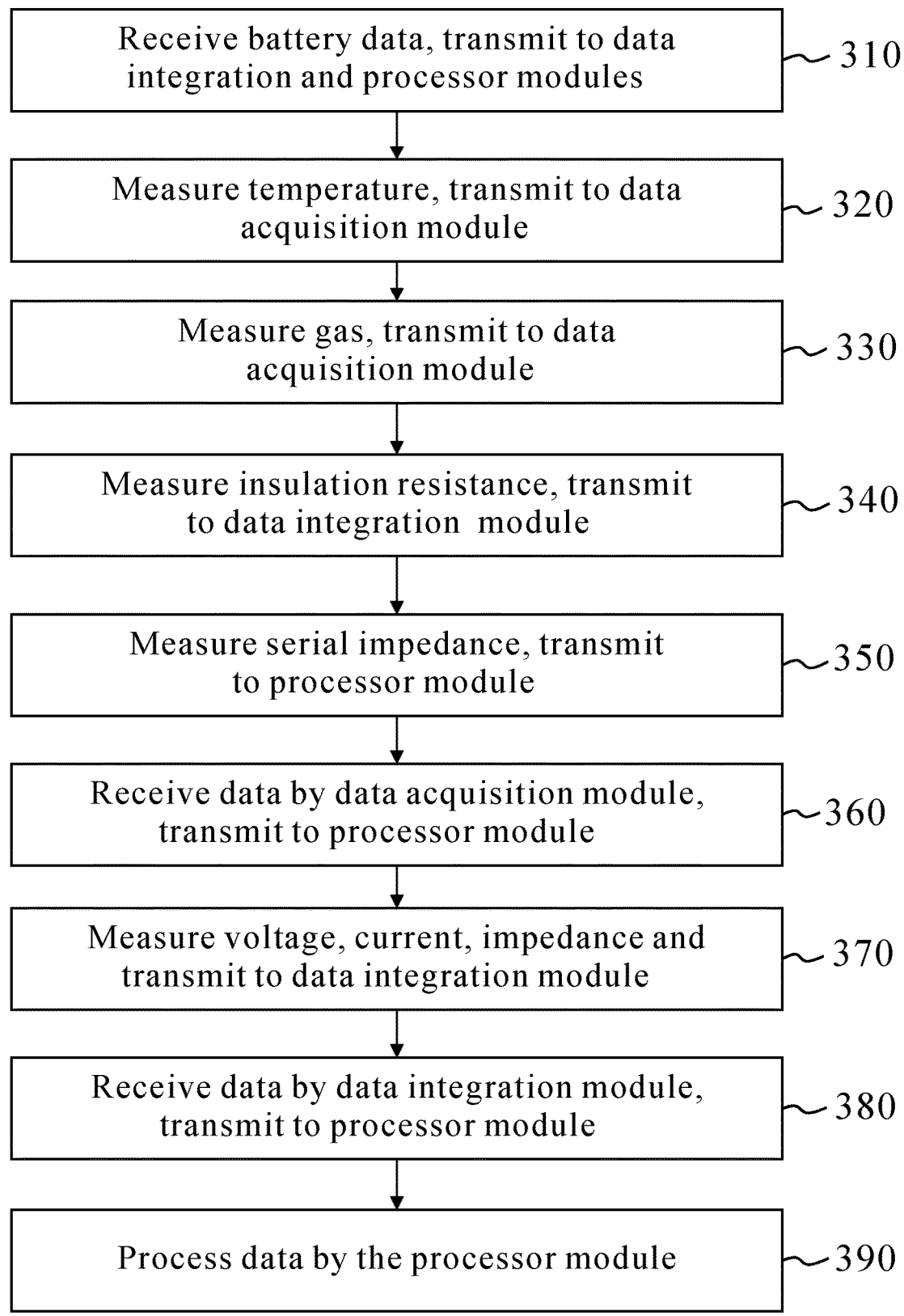
FIG. 4 is a flowchart illustrating a portable battery detection method according to an embodiment of the present disclosure.

Refer to FIG. 4, which is a flowchart illustrating a portable battery detection method according to an embodiment of the present disclosure.

The portable battery detection method 300 comprises in step 310 receiving, by the battery data receiving module, various data of the test battery or data of the battery management system (voltage, current, temperature, SOC, SOH, etc.), and transmitting the data to the data integration module and the processor module.

In step 320, measuring, by the temperature measurement module, the temperature of the test battery and transmitting the temperature data to the data acquisition module.

In step 330, measuring, by the gas measurement module, the gas discharged from the test battery and transferring the gas data to the data acquisition module.

In step 340, measuring, by the insulation resistance measurement module, the insulation resistance value of the battery, and transmitting the insulation resistance value to the data integration module.

In step 350, measuring, by the serial impedance measurement module, the serial impedance value of the battery, and transmitting the serial impedance value to the processor module.

In step 360, receiving, by the data acquisition module, various data sent by the temperature measurement module and the gas measurement module, and transmitting the battery data to the processor module.

In step 370, measuring, by the electric meter module, the battery management system circuit DC voltage, DC current, DC impedance, and transferring the data to the data integration module.

In step 380, receiving, by the data integration module, the data transmitted by the battery data receiving module, the electric meter module, and the insulation resistance measurement module.

In step 390, processing, by the processing module, the received data transmitted by the data integration module, the data acquisition module, the serial impedance measurement module, and the battery data receiving module, and using the processed data to control and manage the operation of the portable battery detection device.

While the present disclosure has been described by means of specific embodiments, numerous modifications and variations could be made thereto by those skilled in the art without departing from the scope and spirit of the present disclosure set forth in the claims.

What is claimed is:

1. A portable battery detection device, comprising:
   a battery data receiving module for receiving various battery data or battery management system data of a battery and transmitting data to a data integration module and a processor module;
   a data acquisition module for receiving various data, and transmitting the various data to the processor module;
   the data integration module for receiving data transmitted by the battery data receiving module and then integrating the data to the processor module;
   the processor module for using data received from the data integration module, the data acquisition module, and battery data receiving module to transmit data, control, and manage the operation of the portable battery detection device, and control a screen to provide a human-machine interface for interaction with the user and provide access to test data; and
   a temperature measurement module for measuring temperature of the battery and transmitting temperature data to the data acquisition module.

2. The portable battery detection device according to claim 1, further comprising:
   a gas measurement module for measuring gas discharged from the battery and transmitting gas data to the data acquisition module.

3. The portable battery detection device according to claim 1, further comprising:
   an insulation resistance measurement module for measuring an insulation resistance value of the battery and transmitting the insulation resistance value to the data integration module.

4. The portable battery detection device according to claim 1, further comprising:
   a serial impedance measurement module for measuring a serial impedance value of the battery and transmitting the serial impedance value to the processor module.

5. The portable battery detection device according to claim 1, wherein the data acquisition module receives various data sent by the temperature measurement module and a gas measurement module, and transmits the various data to the processor module.

6. The portable battery detection device according to claim 1, further comprising:
   an electric meter module for measuring DC voltage, DC current, and DC impedance of a battery management system circuit, and transmitting the DC voltage, DC current, and DC impedance to the data integration module.

7. The portable battery detection device according to claim 1, wherein the data integration module receives data transmitted by the battery data receiving module, an electric meter module, and an insulation resistance measurement module, and then integrates the data to the processor module.

8. The portable battery detection device according to claim 1, wherein the processor module uses data received from the data integration module, the data acquisition module, and a serial impedance measurement module to transmit data, control, and manage the operation of the portable battery detection device, and control the screen to provide a human-machine interface for interaction with the user and provide access to test data.

9. The portable battery detection device according to claim 1, wherein battery data comprises voltage, current, temperature, State Of Charge (SOC), and State Of Health (SOH).

10. The portable battery detection device according to claim 1, wherein the processor module comprises a Raspberry Pi processor.

11. A portable battery detection device, comprising:
a battery data receiving module for receiving various battery data or battery management system data and transmitting data to a data integration module and a processor module;
a temperature measurement module for measuring temperature of a battery and transmitting temperature data to a data acquisition module;
a gas measurement module for measuring gas discharged from the battery and transmitting gas data to the data acquisition module;
an insulation resistance measurement module for measuring an insulation resistance value of the battery and transmitting the insulation resistance value to the data integration module;
a serial impedance measurement module for measuring a serial impedance value of the battery and transmitting the serial impedance value to the processor module;
the data acquisition module for receiving various data sent by the temperature measurement module and the gas measurement module, and transmitting the various data to the processor module;
an electric meter module for measuring DC voltage, DC current, and DC impedance of a battery management system circuit, and transmitting the DC voltage, DC current, and DC impedance to the data integration module;
the data integration module for receiving data transmitted by the battery data receiving module, the electric meter module, and the insulation resistance measurement module, and then integrating the data to the processor module; and
the processor module for using data received from the data integration module, the data acquisition module, and the serial impedance measurement module to transmit data, control, and manage the operation of the portable battery detection device, and control a screen to provide a human-machine interface for interaction with the user and provide access to test data.

12. The portable battery detection device according to claim 11, wherein battery data comprises voltage, current, temperature, State Of Charge (SOC), and State Of Health (SOH).

13. The portable battery detection device according to claim 11, wherein the processor module comprises a Raspberry Pi processor.

14. A portable battery detection method comprising:
receiving, by a battery data receiving module, various battery data of a test battery and transmitting the battery data to a data integration module and a processor module;
measuring, by a temperature measurement module, a temperature of the test battery and transmitting the temperature data to a data acquisition module;
measuring, by a gas measurement module, the gas discharged from the test battery and transferring the gas data to the data acquisition module;
measuring, by an insulation resistance measurement module, an insulation resistance value of the test battery, and transmitting the insulation resistance value to the data integration module;
measuring, by a serial impedance measurement module, a serial impedance value of the battery, and transmitting the serial impedance value to the processor module;
receiving, by the data acquisition module, various data sent by the temperature measurement module and the gas measurement module, and transmitting the battery data to the processor module;
measuring, by an electric meter module, battery management system circuit DC voltage, DC current, DC impedance, and transferring the data to the data integration module;
receiving, by the data integration module, the data transmitted by the battery data receiving module, the electric meter module, and the insulation resistance measurement module; and
processing, by the processing module, received data transmitted by the data integration module, the data acquisition module, the serial impedance measurement module, and the battery data receiving module, and using the processed data to control and manage operation of the portable battery detection device.

15. The portable battery detection device according to claim 14, wherein battery data comprises voltage, current, temperature, State Of Charge (SOC), and State Of Health (SOH).

16. The portable battery detection device according to claim 14, wherein the processor module comprises a Raspberry Pi processor.

17. The portable battery detection device according to claim 14, wherein the processor module comprises a data storage/output module that can output and store analysis data.

18. The portable battery detection device according to claim 17, wherein the data storage/output module stores measurement results in a database mode and outputs corresponding measurement result reports.

19. The portable battery detection device according to claim 18, wherein the measurement results and measurement result reports are accessed by a display or a wireless transfer module.

* * * * *